United States Patent
Wu et al.

(10) Patent No.: US 11,779,529 B2
(45) Date of Patent: *Oct. 10, 2023

(54) PERSONAL CARE COMPOSITION

(71) Applicant: Colgate-Palmolive Company, New York, NY (US)

(72) Inventors: Qiang Wu, Hillsborough, NJ (US); Laurence Du-Thumm, Princeton, NJ (US); Joan Gambogi, Hillsborough, NJ (US); Zeenat Nabi, Cranbury, NJ (US); Cristina Bielli, Hillsborough, NJ (US); Juliana Nwosisi, South Plainfield, NJ (US); Shujiang Cheng, Warren, NJ (US); Halyna Siomyk, Cliffside Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/717,868

(22) Filed: Apr. 11, 2022

(65) Prior Publication Data
US 2022/0233420 A1    Jul. 28, 2022

Related U.S. Application Data

(63) Continuation of application No. 16/771,852, filed as application No. PCT/US2017/065673 on Dec. 12, 2017, now Pat. No. 11,298,306.

(51) Int. Cl.
| | | |
|---|---|---|
| *A61K 8/46* | (2006.01) | |
| *A61K 8/92* | (2006.01) | |
| *A61Q 15/00* | (2006.01) | |

(52) U.S. Cl.
CPC .............. *A61K 8/466* (2013.01); *A61K 8/922* (2013.01); *A61Q 15/00* (2013.01)

(58) Field of Classification Search
None
See application file for complete search history.

(56) References Cited

U.S. PATENT DOCUMENTS

| | | |
|---|---|---|
| 5,871,720 A | 2/1999 | Albanese et al. |
| 7,176,172 B2 | 2/2007 | Harding et al. |
| 8,557,228 B2 | 10/2013 | Pan et al. |
| 8,834,857 B1 | 9/2014 | Winston et al. |
| 9,375,398 B2 | 6/2016 | Dreher |
| 10,285,920 B2 | 5/2019 | Naser et al. |
| 10,300,028 B2 | 5/2019 | Tuffley |
| 10,709,907 B2 | 7/2020 | Pan et al. |
| 2001/0031744 A1 | 10/2001 | Kosbab |
| 2003/0206936 A1 | 11/2003 | Barclay et al. |
| 2007/0003509 A1 | 1/2007 | Rawlings |
| 2008/0124295 A1 | 5/2008 | Duranton et al. |
| 2020/0282240 A1 | 9/2020 | Pan et al. |
| 2021/0169764 A1 | 6/2021 | Wu et al. |

FOREIGN PATENT DOCUMENTS

| | | |
|---|---|---|
| CN | 1494412 | 5/2004 |
| CN | 103429250 | 12/2013 |
| DE | 102013216381 | 2/2015 |
| RU | 2214225 | 10/2003 |
| RU | 2417070 | 4/2011 |
| RU | 2527693 | 9/2014 |
| WO | 2002/096221 | 12/2002 |
| WO | 2008/070368 | 6/2008 |
| WO | 2008/080764 | 7/2008 |
| WO | 2012/103037 | 8/2012 |
| WO | 2013/072852 | 5/2013 |
| WO | 2013/149323 | 10/2013 |
| WO | 2017/196299 | 11/2017 |
| WO | 2019/117858 | 6/2019 |

OTHER PUBLICATIONS

New Roots Herbal, Hair & Scalp: retrieved from on-line website: https://newrootsherbal.com/product/id/1555, Aug. 2016 (Year: 2016).*
International Search Report and the Written Opinion of the International Searching Authority in International Application No. PCT/US2017/065673, dated Mar. 29, 2018.

* cited by examiner

*Primary Examiner* — Kyung S Chang

(57) ABSTRACT

An antiperspirant and/or deodorant composition including from 0.01 weight % to 0.15 weight % flaxseed oil and from 0.5 weight % to 5.0 weight % taurine.

13 Claims, No Drawings

PERSONAL CARE COMPOSITION

CROSS-REFERENCE TO RELATED APPLICATIONS

The present application is a continuation of U.S. patent application Ser. No. 16/771,852, filed Jun. 11, 2020 which is a national stage entry under 35 U.S.C. § 371 of PCT/US2017/065673, filed Dec. 12, 2017, the entireties of which are incorporated herein by reference.

BACKGROUND

Personal care compositions, such as antiperspirant or deodorant compositions and dual purpose antiperspirant-deodorant compositions, may be used to reduce body odor. For example, antiperspirant or deodorant compositions may be applied to axillary (underarm) regions to prevent or treat perspiration, limit the growth of odor-causing bacteria, or apply a fragrance. Further, because antiperspirant or deodorant compositions are applied to the skin, they often include ingredients that provide additional benefits to the skin, such as a reduction in skin irritation.

Collagen is the main structural protein for connective tissue and skin that contributes to skin elasticity and firmness. Without intending to be bound by theory, it is believed that collagen (types I, II, III, IV and V) is synthesized as precursor molecules called procollagens. The procollagens contain additional peptide sequences or "pro-peptides" at both the amino- and carboxy-terminal ends. The function of these pro-peptides is to facilitate the winding of the procollagen molecules into a triple-helical conformation ("triplex helix molecule") within the endoplasmic reticulum. The pro-peptides are cleaved off from the procollagen triplex helix molecule during its secretion as they polymerize into extracellular collagen fibrils. Thus, it should be appreciated that the amount of free pro-peptides stoichiometrically reflects the amount of collagen molecules synthesized, and an increase in collagen production leads to improved skin elasticity and firmness.

Similarly, fibrillin is a glycoprotein which is essential for the formation of elastic fibers found in connective tissue and skin that contributes to skin elasticity and firmness. For example, Fibrillin-1 is a major component of microfibrils that form a sheath surrounding amorphous elastin. Elastin helps skin return to its original shape after it is poked or pinched. Thus, increases in fibrillin production also lead to improved skin elasticity and firmness.

Accordingly, there is a desire for personal care compositions formulated to provide improved skin benefits, and in particular, personal care composition that increase production of procollagen and fibrillin.

BRIEF SUMMARY

This section is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by an antiperspirant and/or deodorant composition, including from 0.01 weight % to 0.15 weight % flaxseed oil, based on a total weight of the antiperspirant and/or deodorant composition; and from 0.5 weight % to 5.0 weight % taurine, based on a total weight of the antiperspirant and/or deodorant composition.

In another embodiment, the antiperspirant and/or deodorant composition includes a 1:10 to 1:30 weight ratio of flaxseed oil to taurine.

In another embodiment, the weight ratio of flaxseed oil to taurine is 1:20.

In another embodiment, the antiperspirant and/or deodorant composition includes from 0.01 weight % to 0.10 weight % flaxseed oil; and from 0.75 weight % to 2.5 weight % taurine.

In another embodiment, the antiperspirant and/or deodorant composition further includes from 30 weight % and 70 weight % of a carrier, based on a total weight of the antiperspirant and/or deodorant composition.

In another embodiment, the antiperspirant and/or deodorant composition further includes from 2.0 weight % and 25 weight % of an antiperspirant and/or deodorant active, based on the total weight of the antiperspirant and/or deodorant composition.

In another embodiment, the antiperspirant and/or deodorant composition further includes from 1.0 weight % and 7.0 weight %, of a surfactant based on the total weight of the antiperspirant and/or deodorant composition.

In another embodiment, the antiperspirant and/or deodorant composition further includes from 0.1 weight % and 10 weight % of an emollient, based on the total weight of the antiperspirant and/or deodorant composition.

In another embodiment, the antiperspirant and/or deodorant composition further includes a fragrance.

In another embodiment, the antiperspirant and/or deodorant composition further includes a preservative and/or an antioxidant.

The foregoing and/or other aspects and utilities embodied in the present disclosure may also be achieved by a method for increasing the production of at least one of fibrillin and procollagen in skin, including applying an antiperspirant and/or deodorant composition to the skin, wherein the antiperspirant and/or deodorant composition includes from 0.01 weight % to 0.15 weight % flaxseed oil, based on a total weight of the antiperspirant and/or deodorant composition; and from 0.5 weight % to 5.0 weight % taurine, based on a total weight of the antiperspirant and/or deodorant composition In another embodiment, the antiperspirant and/or deodorant composition includes a 1:10 to 1:30 weight ratio of flaxseed oil to taurine.

The foregoing and/or other aspects and utilities embodied in the present disclosure may also be achieved by a method for increasing the production of at least one of fibrillin and procollagen in skin, comprising applying the antiperspirant and/or deodorant composition to the skin in an amount sufficient to increase the production of at least one of fibrillin and procollagen.

The foregoing and/or other aspects and utilities embodied in the present disclosure may also be achieved by using the antiperspirant and/or deodorant composition to increase production of at least one of fibrillin and procollagen in skin.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. Phrases such as "in some embodiments," and "in an embodiment" as used herein do not necessarily refer to the same embodiment(s), though they may. Furthermore, the phrases "in another embodiment" and "in certain embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6.0% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether or not "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

As skin ages, the production of collagen and elastin are slowed leading to the formation of wrinkles and the loss of skin elasticity. Enhancing the production of collages and elastin may help reduce the signs of skin aging. The inventors have surprisingly and unexpectedly discovered that mixtures of flaxseed oil (FSO) and taurine have synergistic effects on the production fibrillin and procollagen in skin. Accordingly, the present disclosure provides a personal care composition including synergistic combinations of flaxseed oil and taurine configured to enhanced the production of fibrillin and procollagen in skin. In certain embodiments, the personal care composition may be embodied as an antiperspirant and/or deodorant composition or as a dual antiperspirant-deodorant composition. In other embodiments, the personal care composition may be embodied as a skin lotion or body wash.

The antiperspirant and/or deodorant composition may be provided as a liquid or a gel. For example, the antiperspirant and/or deodorant composition may be a liquid roll-on formulation. The liquid roll-on formulation may be contained in any roll-on dispenser that has an applicator (e.g., ball, roller, etc.) for applying the antiperspirant and/or deodorant composition to surfaces of the skin.

In other embodiments, the antiperspirant and/or deodorant composition may be a solid stick composition. The solid stick composition may be manufactured using conventional methods. For example, the ingredients of a solid stick antiperspirant and/or deodorant composition may be combined and heated to melt the components (other than inert fillers) into a molten mixture. Typically, volatile materials, such as fragrances, are incorporated after heating to avoid volatilization. The molten mixture may then be poured into dispensers, cooled into a solid stick, and capped to preserve the product until use.

The antiperspirant and/or deodorant composition of the present disclosure includes a synergistic combination of flaxseed oil (FSO) and taurine. In certain embodiments, the synergistic combination of flaxseed oil and taurine is configured to enhance the production of fibrillin and procollagen in skin on which the antiperspirant and/or deodorant composition is applied.

The antiperspirant and/or deodorant composition may include from about 0.0001 weight % to about 0.15 weight % flaxseed oil, based on the total weight of the antiperspirant and/or deodorant composition. For example, the antiperspirant and/or deodorant composition may include flaxseed oil in an amount of from about 0.0001 weight % to about 0.10 weight %, from about 0.001 weight % to about 0.10 weight %, from about 0.01 weight % to about 0.10 weight %, from about 0.02 weight % to about 0.07 weight %, from about 0.04 weight % to about 0.10 weight %, or about 0.05 weight %, based on the total weight of the antiperspirant and/or deodorant composition. In one embodiment, the antiperspirant and/or deodorant composition includes about 0.05 weight % flaxseed oil.

Flaxseed oil may be characterized by the amount of alpha-linolenic acid it contains. For example, in one embodiment, the flaxseed oil of the present disclosure contains 50 weight % or more alpha-linolenic acid, based on the total weight of the flaxseed oil.

The antiperspirant and/or deodorant composition may include from about 0.001 weight % to about 5 weight % taurine, based on the total weight of the antiperspirant and/or deodorant composition. For example, the antiperspirant and/or deodorant composition may include from about 0.01 weight % to about 5 weight % taurine, from about 0.1 weight % to about 5 weight % taurine, from about 0.5 weight % to about 5 weight % taurine, from about 0.75 weight % to about 2.50 weight % taurine or from about 0.75 weight % to about 1.25 weight % taurine. In one embodiment, the antiperspirant and/or deodorant composition includes about 1.0 weight % taurine.

In certain embodiments, the amount of flaxseed oil and taurine in the antiperspirant and/or deodorant composition may be provided as a ratio. For example, the antiperspirant and/or deodorant composition may include a 1:5 to 1:30 weight ratio flaxseed oil to taurine. In other examples, the antiperspirant and/or deodorant composition may include a 1:10 to 1:30 weight ratio of flaxseed oil to taurine, 1:5 to 1:25 weight ratio of flaxseed oil to taurine, or 1:10 to 1:25 weight ratio of flaxseed oil to taurine. In one embodiment, the antiperspirant and/or deodorant composition may include a 1:10 to 1:20 weight ratio of flaxseed oil to taurine. For example, the ratio of flaxseed oil to taurine in the antiperspirant and/or deodorant composition may be 1:10, 1:15, 1:20, 1:25, or 1:30. In one embodiment, the ratio of flaxseed oil to taurine in the antiperspirant and/or deodorant composition is about 1:20 flaxseed oil to taurine.

In addition to the combination of flaxseed oil and taurine, the antiperspirant and/or deodorant composition may include additional components. For example, the antiperspirant and/or deodorant composition may include antiperspirant and/or deodorant actives, carriers, and surfactants. The antiperspirant and/or deodorant composition may also include optional ingredients, such as emollients, fragrances, preservatives, antioxidants, colorants, and emulsifiers.

The antiperspirant and/or deodorant composition may include one or more carriers or solvents. For example, the antiperspirant and/or deodorant composition may be provided as an oil-in-water emulsion using water as the carrier. In other embodiments, the carrier may include other co-solvents which are miscible with water. However, in various preferred embodiments, the carrier consists only of water or consists essentially of water, such as a carrier that consists of at least 99% water.

In one embodiment, the amount of carrier in the antiperspirant and/or deodorant composition is the amount to make a 100% by weight composition after all of the ingredients, including any optional ingredients, are added to the composition. For example, the antiperspirant and/or deodorant composition may include at least 20 weight %, at least 30% at least 40 weight %, at least 50 weight %, at least 60 weight %, at least 70 weight %, at least 80 weight %, or at least 90 weight %, of a carrier based on the total weight of the antiperspirant and/or deodorant composition. In other examples, the antiperspirant composition include from about 30 weight % to about 70 weight % water or from about 40 weight % to about 60 weight % water. In one preferred embodiment, the antiperspirant and/or deodorant composition includes about 57 weight % water, based on the total weight of the antiperspirant and/or deodorant composition.

The antiperspirant and/or deodorant composition may include one or more antiperspirant actives. The antiperspirant actives may be selected to be compatible with the other ingredients in the antiperspirant and/or deodorant composition or to maintain specific characteristics thereof. For example, in some embodiments, the antiperspirant actives are selected to maintain an overall pH of the antiperspirant and/or deodorant composition. The antiperspirant actives may include at least one of aluminum chlorohydrate, aluminum chloride, and aluminum zirconium. In one preferred embodiment, the antiperspirant active includes aluminum chloride.

The antiperspirant and/or deodorant composition may include an effective amount of antiperspirant actives. As used herein, the expression or term "effective amount" may refer to an amount of antiperspirant active sufficient to elicit a response (e.g., biological, medical, etc.) when applied to skin. For example, the antiperspirant and/or deodorant composition may include an amount of antiperspirant actives that is effective to reduce the flow of perspiration in the axillary region. In other examples, the antiperspirant and/or deodorant composition may include an amount of antiperspirant actives that is effective to reduce malodor or to act as an antibacterial.

In certain embodiments, the antiperspirant and/or deodorant composition includes from about 2 weight % to about 25 weight % antiperspirant actives, based on a total weight of the antiperspirant and/or deodorant composition. Alternatively, the antiperspirant and/or deodorant composition may include from about 5 weight % to about 20 weight % antiperspirant actives or from about 10 weight % to about 15 weight % antiperspirant actives. For example, in one preferred embodiment, the antiperspirant and/or deodorant composition includes about 12 weight % aluminum chloride.

The antiperspirant and/or deodorant composition may include one or more deodorant actives. In various embodiments, the deodorant actives are selected to be compatible with the other ingredients in the antiperspirant and/or deodorant composition or to maintain specific characteristics thereof. For example, in some embodiments, the deodorant actives are selected to maintain an overall pH of the antiperspirant and/or deodorant composition. In other examples, the deodorant active is selected to be dissolvable in the carrier.

The deodorant actives may include at least one of alum, potassium aluminum sulfate, zinc oxide, ethylhexylglycerin, octenidine hydrochloride, zinc citrate, zinc pyrithione, and silver compounds. For example, the deodorant actives may include potassium aluminum sulfate or potassium aluminum sulfate crystals. In various embodiments, the deodorant actives are fully dissolved in the carrier.

The antiperspirant and/or deodorant composition may include an effective amount of deodorant actives. For example, the antiperspirant and/or deodorant composition may include from about 2 weight % to about 25 weight % deodorant actives, based on a total weight of the antiperspirant and/or deodorant composition. In other examples, the antiperspirant and/or deodorant composition may include from about 10 weight % to about 20 weight % deodorant actives or from about 8 weight % to about 16 weight % deodorant actives. In one preferred embodiment, the antiperspirant and/or deodorant composition includes about 12 weight % deodorant actives.

The antiperspirant and/or deodorant composition may include one or more surfactants. The surfactants may be selected to provide adequate viscosity to the antiperspirant and/or deodorant composition. The surfactants may also be selected to enable the solubilization of other ingredients in the antiperspirant and/or deodorant composition. The surfactants may further be selected to resist degradation in a low pH environment. For example, the one or more surfactants may include at least one of Steareth-2, Steareth-4, Steareth-6, Steareth-7, Ceteareth-2, Ceteareth-3, Ceteareth-4, Ceteareth-5, Steareth-21, Steareth-10, Steareth-11, Steareth-13, Steareth-15, Steareth-20, Ceteareth-6, Ceteareth-7, Ceteareth-8, Ceteareth-9, Ceteareth-10, Ceteareth-11, and Ceteareth-12. In a preferred embodiment, the one or more surfactants include Steareth-20 and Steareth-2.

In some embodiments, the antiperspirant and/or deodorant composition may include surfactants in an amount of from about 1 weight % to about 7 weight %, based on a total weight of the antiperspirant and/or deodorant composition. For example, the antiperspirant and/or deodorant composition may include from about 2 weight % to about 6 weight % surfactants. In one preferred embodiment, the antiperspirant composition may include about 3.5 weight % surfactants. For example, the antiperspirant and/or deodorant composition may include about 1.2 weight % Steareth-20 and about 2.3 weight % Steareth-2 as surfactants.

The antiperspirant and/or deodorant composition may include one or more emollients. For example, the antiperspirant and/or deodorant composition may include non-volatile emollients in any desired amount to achieve a desired emollient effect. Emollients are known in the art and are used to impart a soothing effect on the skin. Classes of non-volatile emollients include non-silicone and silicone emollients. Non-volatile, non-silicone emollients include C12-15 alkyl benzoate. Non-volatile siliconeemollinets can be a polyethersiloxane, polyalkyarylsiloxane or polyethersiloxane copolymer. Non-limiting examples of emollients can be found in U.S. Pat. No. 6,007,799. Examples include, but are not limited to, PPG-14 butyl ether, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl bras sylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, alkyl benzoate, hydrocyethyl stearate amide, and hydrogenated polyisobutene.

In one embodiment, the emollient may be selected from linear silicones, cyclic silicones, hydrocarbons, polyhydroxy alcohols having more than carbon atoms, liquid or solid polyalkyleneglycol ethers containing a polypropylene glycol (PPG) moiety and terminating in an alkyl ether, and combinations thereof. In another embodiment, the emollient is a nonvolatile silicone, such as dimethiconol or a longer chain dimethicone.

The antiperspirant and/or deodorant composition may include from about 0.1% to about 10% emollients, based on a total weight of the antiperspirant and/or deodorant composition. For example, the antiperspirant and/or deodorant composition may include from about 1 weight % to about 5 weight % emollients or from about 2 weight % to about 4 weight % emollients.

The antiperspirant and/or deodorant composition may include one or more preservatives. The preservatives may improve an antimicrobial characteristic of the antiperspirant and/or deodorant composition to improve storage life or prevent decay. The preservatives may also enhance the functional characteristics of the antiperspirant and/or deodorant composition. For example, the preservative may enhance deodorant or emollient effects to the antiperspirant and/or deodorant composition.

Illustrative preservatives may include, but are not limited to, at least one of phenoxyethanol, BHT (butylated hydroxytoluene), Ethylenediaminetetraacetic acid (EDTA), caprylyl glycol, ethylhexylglycerin, citric acid, benzoic acid, lactic acid, and combinations thereof.

The antiperspirant and/or deodorant composition may include an effective amount of preservatives. For example, the antiperspirant and/or deodorant composition may include an amount of preservatives effective to reduce a spoilage of the antiperspirant and/or deodorant composition during storage or use.

In some embodiments, the antiperspirant and/or deodorant composition may optionally include one or more fragrances. A variety of fragrances may be used in the antiperspirant and/or deodorant compositions if a scented product is desired. For example, any fragrance suitable for personal care use may be incorporated into the antiperspirant and/or deodorant composition as a non-essential ingredient.

Examples

Aspects of the present disclosure may be further understood by referring to the following examples. The examples are illustrative, and are not intended to be limiting embodiments thereof. Table 1 illustrates a base roll-on antiperspirant composition. The base roll-on antiperspirant composition of Table 1 was used to create the three comparative roll-on antiperspirant compositions of Tables 2 and 3 incorporating varying amounts of flaxseed oil and taurine according to embodiments of the present disclosure.

Table 2 illustrates comparative measures of Fibrillin-1 and procollagen concentrations of the three comparative roll-on antiperspirant composition against the base roll-on antiperspirant composition of Table 1 as a control and an untreated sample as measured through a reconstructed skin tissue culture.

Table 3 illustrates comparative measures of collagen I concentration in the three comparative roll-on antiperspirant composition against an untreated sample as measured through a monolayer skin cultures

TABLE 1

| Base roll-on composition | |
| --- | --- |
| Water | 58.94% |
| Caprylyl glycol | 0.3% |
| Steareth-20 | 1.2% |

TABLE 1-continued

Base roll-on composition

| | |
|---|---|
| PPG-15 stearyl ether | 1.56% |
| BHT | 0.05% |
| Steareth-2 | 2.3% |
| Hydrogenated Soybean Oil | 3% |
| EDTA | 0.25% |
| Aluminum Chloride (40%) | 30% |
| Mayaflor (fragrance) | 2.4% |

Each of the compositions of Table 2 were tested on full-thickness human skin equivalent models (EFT-400, available from MATTEK Corp., Ashland, Mass.) as follows: normalized tissue samples (EFT-400) were placed in 6-well plates with 1 ml of fresh media. 30 μL of each composition (control composition and compositions 1-3) were evenly added on top of each tissue sample, and some samples were left untreated. The tissue samples were incubated at 37° C. for 60 minutes and a media sample (supernate) was collected and stored at −80° C. for later testing. After incubation, the tissue samples were washed with phosphate buffer saline (PBS) to remove the compositions and then transferred into new plates with 1 ml new media.

To evaluate fibrillin-1 and procollagen production, the supernate media samples collected at 1 and 48 hours were tested using ELISA kits for human fibrillin-1 (FBN1) (CSB-E 13141h, CUSABIO) and Procollagen Type I C-peptide (PIP) (MK101, TAKARA), respectively. The testing was done in triplicate and the data in Table 2 represents the average value for 3 tests.

TABLE 2

| | Untreated | Control Composition | Composition 1 | Composition 2 | Composition 3 |
|---|---|---|---|---|---|
| Base roll on formula | — | 100% | 99% | 99.95% | 98.95% |
| Taurine | — | — | 1.0% | — | 1.0% |
| Flaxseed oil | — | — | — | 0.05% | 0.05% |
| Total | — | 100% | 100% | 100% | 100% |
| FBN1 concentration (1 hr.) | 66.14 ng/ml | 82.33 ng/ml | 370.74 ng/ml | 59.57 ng/ml | 538.81 ng/ml |
| FBN1 concentration normalized based on Control | | | 288.41 ng/ml | −22.76 ng/ml | 456.48 ng/ml |
| Procollagen Type 1 C-peptide (PIP) concentration (1 hr.) | 12.3 ng/ml | 43.4 ng/ml | 59.7 ng/ml | 47.8 ng/ml | 79.1 ng/ml |
| Procollagen Type 1 C-peptide concentration normalized based on Control | | | 16.3 ng/ml | 4.4 ng/ml | 35.7 ng/ml |

As illustrated in Table 2, the combination of flaxseed oil and taurine in composition 3 demonstrates synergistic effects for the production of fibrillin-1 and procollagen.

Each of the compositions of Table 3 was tested on human dermal fibroblast cells (Thermo Fisher Scientific, Gaithersburg, Md.) as follows: human dermal fibroblast cells were seeded in 6-well plates and grow until about 80% confluency. 1 mL of each composition was added to the wells in triplicate per composition. The cells were then incubated at 37° C., 5% $CO_2$ for 24 hours and the supernatants were collected and analyzed for Collagen I release. Collagen I release in the supernatants was measured using COL1A1 ELISA kit (MyBioSource, San Diego, Calif.). The average Collagen I release per composition was calculated and is shown in Table 3. The data in Table 3 represents the average value for 3 tests.

TABLE 3

| Composition | Collagen I (ng/ml) | Standard deviation (ng/ml) |
|---|---|---|
| Solvent Only (Control) | 0.7 | 0.3 |
| Solvent + 0.001% Taurine | 1.9 | 0.7 |
| Solvent + 0.0001% Flaxseed Oil | 0.3 | 0.1 |
| Solvent + 0.001% Taurine + 0.0001% Flaxseed Oil | 4.2 | 0.9 |

As illustrated in Table 3, the combination of taurine and flaxseed oil demonstrates synergistic effects in promoting Collagen I production as compared to the individual effects taurine and flaxseed oil alone.

Accordingly, as shown by Tables 2-3, the inventors have surprisingly discovered a new antiperspirant and/or deodorant composition which enhances production of fibrillin-1 and procollagen and could provide the anti-aging skin benefits of increasing skin elasticity and firming.

The present disclosure has been described with reference to exemplary embodiments. Although a limited number of embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. A personal care composition, comprising:
   from 0.5 weight % to 5 weight % taurine; and
   from 0.01 weight % to 0.15 weight % flaxseed oil, based on a total weight of the personal care composition;
   wherein the flaxseed oil and the taurine are present in a 1:10 to 1:30 weight ratio of flaxseed oil to taurine, and the flaxseed off and taurine synergistically increase the production of at least one of fibrillin-1 and procollagen in skin.

2. The personal care composition according to claim 1, wherein the personal care composition is selected from an antiperspirant and/or deodorant composition, a skin lotion and a body wash.

3. The personal care composition according to claim 2, wherein the personal care composition is a skin lotion.

4. The personal care composition according to claim 2, wherein the personal care composition is a body wash.

5. The personal care composition according to claim 2, which is the antiperspirant and/or deodorant composition, comprising from 0.01 weight % to 0.10 weight % flaxseed oil; and from 0.75 weight % to 2.5 weight % taurine.

6. The personal care composition of claim 1, wherein the weight ratio of flaxseed oil to taurine is 1:20.

7. The personal care composition of claim 5, further comprising from 30 weight % and 70 weight % of a carrier, based on a total weight of the antiperspirant and/or deodorant composition.

8. The personal care composition of claim 5, further comprising from 2.0 weight % and 25 weight % of an antiperspirant and/or deodorant active, based on the total weight of the antiperspirant and/or deodorant composition.

9. The personal care composition of claim 8, further comprising from 1.0 weight % and 7.0 weight %, of a surfactant based on the total weight of the antiperspirant and/or deodorant composition.

10. The personal care composition of claim 9, further comprising from 0.1 weight % and 10 weight % of an emollient, based on the total weight of the antiperspirant and/or deodorant composition.

11. The personal care composition of claim 10, further comprising a fragrance.

12. The personal care composition of claim 11, further comprising a preservative and/or an antioxidant.

13. A method for increasing the production of at least one of fibrillin and procollagen in skin, comprising applying a personal care composition to the skin, wherein the personal care composition comprises:
   from 0.01 weight % to 0.15 weight % flaxseed oil; and
   from 0.5 weight % to 5.0 weight % taurine, based on a total weight of the personal care composition;
   wherein the flaxseed oil and the taurine are present in a 1:10 to 1:30 weight ratio of flaxseed oil to taurine, and the flaxseed oil and taurine synergistically Increase the production of at least one of fibrillin-1 and procollagen in skin.

* * * * *